United States Patent [19]

LeVeen

[11] Patent Number: 4,569,946
[45] Date of Patent: Feb. 11, 1986

[54] TREATMENT WITH DIALDEHYDES

[76] Inventor: Harry H. LeVeen, 800 Poly Pl., Brooklyn, N.Y. 11209

[21] Appl. No.: 244,056

[22] Filed: Mar. 16, 1981

Related U.S. Application Data

[63] Continuation of Ser. No. 24,028, Mar. 26, 1979, Pat. No. 4,256,768, which is a continuation of Ser. No. 863,443, Dec. 22, 1977, abandoned, which is a continuation of Ser. No. 680,714, Apr. 27, 1976, abandoned, which is a continuation-in-part of Ser. No. 678,955, Apr. 21, 1976, abandoned.

[51] Int. Cl.$^4$ ............................................. A61K 31/11
[52] U.S. Cl. .................................................... 514/693
[58] Field of Search ......................... 424/333; 514/693

[56] References Cited

U.S. PATENT DOCUMENTS 2,801,216  7/1957  Yoder et al. .......................... 424/333
3,983,252  9/1976  Buchalter ............................ 424/333
4,082,852  4/1978  Heiss .................................... 424/333

OTHER PUBLICATIONS

Stock et al., Cancer Research, vol. 18, No. 8, Sep. 1958, pp. 49-53 and 182.
Leiter et al., Cancer Research, vol. 23, No. 8, Sep. 1963, pp. 1483-1495, 1498 and 1595.
Leiter et al., Cancer Research, vol. 23, No. 10, Nov. 1963, pp. 1930-1941, 1944, 1945 and 1984.

*Primary Examiner*—Jerome D. Goldberg
*Attorney, Agent, or Firm*—Gipple & Hale

[57] ABSTRACT

Lower aliphatic dialdehydes have been found to react with human and other animal tissues in the living animal and that treatment of exposed tissue by topical application is useful in converting "wet" gangrene to "dry" gangrene, in forming a protective eschar for burned tissue, and for treating the raw, cut portions of the body during surgical excision of malignant tumors to prevent growth of implants resulting from dissemination of malignant cells during the excision. Threatment is generally by topical application of the dialdehyde diluted, typically, to 1 or 2 percent in a fluent carrier such as water or alcohol.

7 Claims, No Drawings

TREATMENT WITH DIALDEHYDES

RELATED APPLICATION

This application is a continuation of LeVeen application Ser. No. 24,028, filed Mar. 26, 1979, now U.S. Pat. No. 4,256,768, which is a continuation of LeVeen application Ser. No. 863,443, filed Dec. 22, 1977, now abandoned, which is a continuation of LeVeen application Ser. No. 680,714, filed Apr. 27, 1976, entitled TREATMENT WITH DIALDEHYDES, now abandoned, which in turn is a continuation-in-part of LeVeen application Ser. No. 678,955, filed Apr. 21, 1976, entitled TREATMENT WITH GLUTARALDEHYDE, now abandoned.

This invention relates to the treatment of human and other animal tissue of a living animal and in particular provides a process for treating the surface of exposed tissue to alter the nature of the tissue in a manner having beneficial results in a variety of applications.

One important object of the present invention is to provide a process for treating "wet" gangrene in order to convert it to "dry" gangrene.

It is a further object of this invention to provide a process for the treatment of burns which will promote the healing of the burns, and which in the case of extensive burns such as third degree burns, can assist in lowering the fatality rate.

It is a further object of this invention to provide a process for treating raw tissue exposed during surgical excision of malignant tumors which is effective in reducing the recurrence of the tumor by implant due to dissemination of malignant cells during the excision.

These and other objects of the present invention are obtained by topical application to the exposed surface of the tissue to be treated with lower aliphatic dialdehydes diluted in a suitable, pharmaceutically acceptable carrier and is based on the discovery that such dialdehydes, although moderately toxic and irritating, when suitably diluted will effectively and safely react with animal tissue in the living animal to alter its nature in a way promoting the above objects. It has also been found that aliphatic dialdehydes have germicidal and sporicidal properties which are consistent with the above objects.

It has heretofore been known that glyoxal and gluteraldehyde will cause cross-linking of protein molecules to convert them to a stable polymer. Apparently, the same chemical reactions take place with human and other animal tissue in the living animal.

In accordance with the present invention, the application of the dialdehyde is made directly and topically to the surface of the tissue to be treated, suitably diluted in a pharmaceutically acceptable carrier from 0.1% up to about 10% by weight of the dialdehyde. Preferably, the dilution is on the order of 1 or 2% for topical application to exterior portions of the body and 1% where the application is to surgically exposed internal parts of the body.

Gluteraldehyde is infinitely soluble in water and ethyl alcohol, and the preferred pharmaceutical carriers for it are water and water/alcohol mixtures such as 70% ethyl alcohol. For internal application, the preferred carriers are water and saline.

Glyoxal, which is very soluble in water, is also preferably diluted in water or saline as a carrier. Glyoxal is available commercially in 40% aqueous solutions which contain a polymerization inhibitor and can be used simply by diluting further with water.

Succinaldehyde, which is only slightly soluble in alcohol and water and adipaldehyde, which is insoluble in water but very soluble in alcohol, can be used in aqueous systems as suspensions, but also where continuous application is desired can be incorporated in ointments and the like. The relatively water-insoluble dialdehydes have the additional advantage in that tissue penetration is limited and the possibility of toxicity problems is thereby reduced.

Treatment of Gangrene

A smelly, infected ischemic ulceration of the foot is treated by a continuous soak of the infected area with a 1% solution of gluteraldehyde either in water or in 70% ethyl alcohol until the ulceration is converted to a dry, coagulation type of necrosis that is seen when the arterial blood supply of an extremity is compromised without infection. In this situation, the gangrenous part can frequently be left for auto-amputation. Active infection of an ischemic extremity ordinarily requires amputation at a considerably higher level in the limb in order to rid the body of infection and assure that the amputation is performed through healthy, viable tissue capable of healing. The conversion of "dry" gangrene, on the other hand, is like the coagulation necrosis which occurs with arterial insufficiency unassociated with infection. This is especially important in diabetic gangrene, where "moist" gangrene is frequently encountered because of the lowered resistance of diabetics to infection.

Treatment of Burns

Burned and weeping tissue is converted to a leather-like eschar which is intimately attached to the underlying tissue by the application to the surface of the burn of a 2% solution of gluteraldehyde in water. Application is made topically with a continuous soak until the protective eschar is formed. As epitheliazation takes place, the eschar is lifted and drops off in the same manner as a natural scab. Application in this manner with third degree burns in mice has been found to lower the fatality rate in extensive body burns.

Treatment during Surgery

In the surgical excision of malignant tumors and also in incision for the purpose of a biopsy, it is not infrequent that the tumor is incised or broken into either by error or purposefully. In such a case, malignant cells can be disseminated onto adjacent normal tissue with resultant growth of implants. Also, during surgical excision of carcinoma, in some cases it is not possible to clamp the blood supply prior to dissection. This happens, for example, in an abdomino-perineal resection, in which case the rectum is scooped from the hollow of the secrum and pelvis and there is little possibility of prior ligation of the blood supply to the bowel containing the tumor. The venous blood draining the area of the malignant tumor is loaded with carcinoma cells. When ligation of the blood supply is not possible prior to manipulation and removal of the tumor, tumor cells from the venous blood will enter the wound. Incidence of perineal recurrence after an abdomino-perineal resection is about 15%.

Seeding of malignant cells is also highly probable during intestinal anastomosis. The two cut ends of the bowel which are resected to remove the carcinoma are anastomosed to each other and are highly susceptible to implants at these cut ends. The pathenogenesis of this type of implant results from the fact that there are free floating tumor cells in the bowel lumen, and the cut edge of the mucosa where the bowel is anastomosed exposes the underlying tissue to these cells and such cut surfaces are fertile sites for implantation. The free floating tumor cells arise from the shedding of cells of the intra-luminal cancer.

Other types of surgical excision of malignant tumors also provide opportunities for seeding the open wound, thus defeating the excision of the tumor.

In accordance with this invention, the raw tissue surfaces after surgical excision of a malignant tumor are rendered inhospitable to the growth of tumor implants by topical application of diluted gluteraldehyde, for example, by painting the raw, exposed surfaces with a 1% solution of gluteraldehyde in water or saline. Experiments have been done with mouse ascites carcinoma. A skin flap was raised on the back of each mouse and four to five drops of tumorcontaining ascitic fluid was dropped on the raw surface after reflection of the skin. In control animals, the area was washed with saline to remove any malignant cells. In the control group, fifty percent of the animals developed implant carcinoma, whereas animals treated with 1% gluteraldehyde did not develop an implant. Painting the cut edges of colon during bowel anastomosis prevented suture line recurrences in rabbits given intraluminal injections of Brown Pierce Tumor. Similar results were obtained in squamous cell and intestinal cancer in humans where 1% gluteraldehyde in water totally prevented implantation. One percent gluteraldehyde was used in abdomino-perineal resections by wetting the cut surface of the bowel with the gluteraldehyde solution on moistend pads. No implants occured in patients who have had the gluteraldehyde treatment. The incidence of recurrent cancer at the suture line in human bowel cancer can be significantly reduced. Furthermore, the gluteraldehyde did not impair wound healing and there has been no evidence of any complications, either as to healing or general toxicity. Similar treatment has been used in human peritoneal cavities during biopsy of tumors, when inadvertent breaking into of tumors occurred and after total removal of tumors, when spillage might have occurred, with no adverse effects nor implant of carcinoma.

Other lower aliphatic dialdehydes such as glyoxal, succinaldehyde, adipaldehyde, and suberaldehyde are substituted for gluteraldehyde with similar results.

I claim:

1. A method of treatment of tissue in a living animal exposed during surgical removal of malignant tissue which comprises applying to the surface thereof a lower aliphatic dialdehyde selected from the group consisting of glyoxal, gluteraldehyde, adipaldehyde, succinaldehyde and suberaldehyde diluted from 0.1% up to about 10% by weight in a pharmaceutically acceptable carrier.

2. A method according to claim 1 in which the proportion of dialdehyde is up to 10% by weight of the carrier.

3. The method according to claim 1 in which the dialdehyde is gluteraldehyde.

4. The method according to claim 1 in which the dialdehyde is succinaldehyde.

5. The method according to claim 1 in which the dialdehyde is glyoxal.

6. The method according to claim 1 in which the dialdehyde is adipaldehyde.

7. The method according to claim 1 in which the dialdehyde is suberaldehyde.

* * * * *